(12) United States Patent
Kirsch et al.

(10) Patent No.: US 10,899,852 B2
(45) Date of Patent: Jan. 26, 2021

(54) BENZIL MONOKETALS AND THE USE THEREOF

(71) Applicant: Merck Patent GmbH, Darmstadt (DE)

(72) Inventors: Peer Kirsch, Seeheim-Jugenheim (DE); Qiong Tong, Darmstadt (DE); Alexander Hahn, Biebesheim (DE); Leo Weegels, Darmstadt (DE); Steffen Gnauck, Darmstadt (DE); Sven Schuepfer, Aschaffenburg (DE); Peter Leonhard, Darmstadt (DE); Claudia Enders, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 351 days.

(21) Appl. No.: 15/769,826

(22) PCT Filed: Oct. 5, 2016

(86) PCT No.: PCT/EP2016/001648
§ 371 (c)(1),
(2) Date: Apr. 20, 2018

(87) PCT Pub. No.: WO2017/067634
PCT Pub. Date: Apr. 27, 2017

(65) Prior Publication Data
US 2020/0247916 A1 Aug. 6, 2020

(30) Foreign Application Priority Data
Oct. 23, 2015 (DE) .......................... 10 2015 013 754

(51) Int. Cl.
*C08F 2/46* (2006.01)
*C08F 2/50* (2006.01)
*C08G 61/04* (2006.01)
*C07C 49/84* (2006.01)
*G02F 1/1339* (2006.01)

(52) U.S. Cl.
CPC ............... *C08F 2/46* (2013.01); *C07C 49/84* (2013.01); *G02F 1/1339* (2013.01); *G02F 2202/023* (2013.01)

(58) Field of Classification Search
CPC . G02F 1/1339; G02F 2202/023; C07C 49/84; C08F 2/46
USPC ........... 522/44, 33, 6, 71, 189, 184, 1; 520/1
See application file for complete search history.

(56) References Cited

U.S. PATENT DOCUMENTS

| 8,216,353 | B2 | 7/2012 | Nakamura |
| 9,714,353 | B2 | 7/2017 | Yofu |
| 2008/0241424 | A1 | 10/2008 | Nakamura |
| 2009/0147206 | A1 | 6/2009 | Lee et al. |
| 2009/0169765 | A1* | 7/2009 | Nakamura ........... C09D 11/324 427/511 |
| 2015/0353748 | A1 | 12/2015 | Yofu |

FOREIGN PATENT DOCUMENTS

| EP | 1975214 A1 * | 10/2008 | ........... C09D 11/101 |
| EP | 1975214 A1 | 10/2008 | |
| WO | 2014/148290 A1 | 9/2014 | |

OTHER PUBLICATIONS

International Preliminary Report on Patentability dated Apr. 24, 2018 issued in corresponding PCT/EP2016/001648 application (6 pages).
International Search Report dated Dec. 7, 2016 issued in corresponding PCT/EP2016/001648 application (2 pages).

\* cited by examiner

*Primary Examiner* — Jessica Whiteley
(74) *Attorney, Agent, or Firm* — Millen, White, Zelano and Branigan, P.C.

(57) ABSTRACT

The present invention relates to the use of hydrophilic compounds of the formula I as photopolymerisation initiators of polymerisable substance mixtures which comprise unsaturated compounds, or for the photochemical crosslinking of linear polymers,

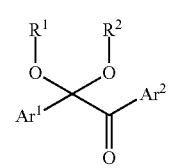

in which the parameters have the meaning indicated in Claim 1, to sealants for liquid-crystal displays which comprise the hydrophilic photoinitiators, to novel hydrophilic photoinitiators of the formula I, and to the liquid-crystal displays produced using these sealants.

11 Claims, No Drawings

BENZIL MONOKETALS AND THE USE THEREOF

The present invention relates to the use of hydrophilic benzil monoketals as photoinitiators in heat- and light-curing sealants, to the use of these sealants in a one drop filling (ODF) process for the production of liquid-crystal displays, to sealants which comprise the hydrophilic photoinitiators, to novel hydrophilic photoinitiators, and to the liquid-crystal displays produced using these sealants.

Liquid crystals have found a broad range of applications since the first commercially usable liquid-crystalline compounds were found about 30 years ago. Known areas of application were initially, in particular, displays for watches and calculators, before the first displays for, for example, portable and desktop computers came out.

The increasing popularity of liquid-crystal display devices (LCDs) resulted in rapid technical development and is attributable, in particular, to the fact that LCDs, compared with the previously prevailing technology of cathode ray tubes, have low power consumption, a lightweight design and low thickness and do not emit any harmful electromagnetic radiation. LCD devices have also attracted considerable attention owing to the use as large-area displays for, inter alia, television sets, initially together with plasma display panels (PDPs), having screen sizes of up to 50 inches or more.

The LCD device itself comprises two substrates with electrodes and a layer of the liquid crystal located in the space enclosed by the substrates. The display of an image is achieved by changing the alignment of the liquid crystals with the aid of an electric voltage applied to the electrodes.

An LCD display is typically produced by adhesively bonding a first substrate having a pixel electrode, a thin-film transistor (TFT) and other components to a second substrate which contains a common electrode, using a sealant.

The space enclosed by the substrates is filled with the liquid crystal via a fill opening by means of capillary force or vacuum; the fill opening is subsequently sealed using a sealant.

With the increase in the size of liquid-crystal displays in recent years, the so-called "one drop filling" process (ODF process) has been proposed as a process for the mass production of liquid-crystal displays (see, for example, JPS63-179323 and JPH10-239694) in order to shorten the cycle times during production. This is a process for the production of a liquid-crystal display in which a drop of the liquid crystal is applied to the substrate, which is fitted with electrodes and is provided with a sealant round the edges. The second substrate fitted with electrodes is subsequently mounted in vacuo, the sealant is partially cured by UV irradiation and subsequently fully cured by heat treatment. The two-step process consisting of UV curing and thermal curing enables the duration of curing to be shortened.

However, this process has the disadvantage that the sealant in the uncured state comes into contact with the liquid crystal and the constituents of the sealant are able to diffuse into the liquid crystal.

In the case of the ODF process, a distinction is made between three processes:
a heat-curing process, a photocuring process and a photocuring and heat-curing process for the curing of a sealant for liquid crystals after the two substrates have been joined together. The disadvantage of the heat-curing process is that the liquid crystal expands and as a consequence of the heating its viscosity drops, which favours mixing with the sealant.

In the photocuring process, a distinction is made between two types of sealant, those of the cation polymerisation type and those of the free-radical polymerisation type, in each case depending on the type of photopolymerisation initiator. In the case of sealants of the cationic polymerisation type, the problem exists that ions are generated during the photocuring which are able to diffuse into the liquid crystal, which results in a decrease in the specific resistance of the liquid crystal. In the case of sealants of the free-radical polymerisation type, the problem exists that the curing shrink-age is relatively large, which can result in low strength of the adhesion. Both types of sealant, i.e. both of the cationic polymerisation type and of the free-radical polymerisation type, have the joint problem that shaded parts which are not irradiated with light remain uncured or only incompletely cured, for example behind metal contacts of electronic components of the TFT array substrate of the liquid-crystal display or behind the black matrix of the colour-filter substrate.

The photocuring and heat-curing process has therefore proven particularly suitable in practice. This is characterised in that the sealant for liquid crystals between the substrates is subjected to primary curing by irradiation with light, followed by a secondary curing step by heating. It is essential in the photocuring and heat-curing process that the liquid crystal is not contaminated either before or after the exposure to light or before or after the heating. What is needed, in particular, are measures for curing the shaded areas mentioned above and measures for preventing diffusion of constituents of the sealant during the heat curing.

Suitable starting points for a solution are rapid curing at low temperature before commencement of mixing of the sealant with the liquid crystal or the use of components in the sealant which dissolve less in the liquid crystal or not at all. Rapid curing at low temperature means that the life of the sealant is very short owing to the high reactivity, which represents a major problem in practice. Preference is therefore given to the use of sealants which have a long life and comprise components which have low solubility in the liquid crystal.

Sealants for liquid-crystal displays are disclosed, for example, in US2007/096056 A1, EP 1780587 A1, US 2003/0147034 A1 and EP 2381304 A1.

In order to reduce the solubility of the sealants in the highly non-polar liquid crystal, sealants have been proposed based on polar epoxy resins and polar acrylic resins which contain alcoholic hydroxylic groups or sulfone groups, as described, for example, in WO 2004/104683, EP 1559735 A1 and US 2008/0305707.

The problems described above of damage to the liquid crystal during curing of sealants for liquid-crystal displays are severe, in particular, if the liquid crystal itself comprises polymerisable components: this is the case in a relatively new display mode, so-called PS ("polymer sustained") or PSA ("polymer sustained alignment") mode, which is occasionally also called polymer stabilised. In PSA displays, a liquid-crystal medium is used which consists of a liquid-crystal host and a small amount—typically <1% by weight—of one or more polymerisable compounds. After the display has been filled, the polymerisable compounds are polymerised and crosslinked in situ, usually by UV irradiation and with application of a voltage. Polymerisable liquid crystals have proven particularly suitable as reactive components, so-called reactive mesogens (RMs).

The PSA mode is in the meantime being used in various conventional types of LCD, such as, for example, PS-VA ("vertically aligned"), PS-OCB ("optically compensated bend"), PS-IPS ("in-plane-switching"), PS-FFS ("fringe field switching"), and PS-TN ("twisted nematic"). The polymerisation of the RMs is preferably carried out with application of a voltage in the case of PS-VA and PS-OCB displays, and with or without, preferably without, an applied voltage in the case of PS-IPS displays, producing a pre-tilt angle of the LC molecules in the display cell. In the case of PS-OCB displays, for example, it is possible to stabilise the curve structure, meaning that an off-set voltage is unnecessary or can be reduced. In the case of PS-VA displays, the pre-tilt has a positive effect on the response times. These examples make it clear that polymer stabilisation has a considerable influence on the sensitive processes during switching and that the polymerisation must proceed under extremely controlled conditions. Contamination of the liquid crystal with components of the sealant during production is therefore critical, particularly in the case of PSA displays, since this results in uncontrolled reactions of the RMs and consequently in clearly visible display defects owing to local misalignment of the liquid-crystal molecules.

PS-VA displays area described, for example, in EP1170626 A2, U.S. Pat. Nos. 6,861,107, 7,169,449, US2004/0191428A1, US2006/0066793A1 and US2006/0103804A1. PS-OCB displays are described, for example, in T.-J. Chen et al., Jpn. J. Appl. Phys. 45, 2006, 2702-2704 and S. H. Kim, L.-C. Chien, Jpn. J. Appl. Phys. 43, 2004, 7643-7647. PS-IPS displays are described, for example, in U.S. Pat. No. 6,177,972 and Appl. Phys. Lett. 1999, 75(21), 3264. PS-TN displays are described, for example, in Optics Express 2004, 12(7), 1221.

The photoinitiators employed in sealants for liquid crystals are particularly problematic since, after activation, they liberate the actual reactive free radicals which initiate or accelerate the polymerisation and which, as small molecules, have high mobility and are usually readily soluble in liquid crystals.

US 2009/0147206 proposes polymeric photoinitiators which, owing to their polymer structure based on a polyacrylate, are intended to remain in the sealant during curing. A disadvantage here is that large polymeric photoinitiators have low mobility, and, owing to the fact that they are prepared by polymerisation of a monomer precursor, particularly reactive types of initiator are only accessible with difficulty.

The object of the present invention is therefore to provide photoinitiators for use in sealants for liquid-crystal displays which do not have the above-mentioned disadvantages or only do so to a small extent.

Surprisingly, it has been found that this object can be achieved by using photoinitiators of the formula I.

The invention therefore relates to the use of compounds of the formula I as photopolymerisation initiators of polymerisable substance mixtures which comprise unsaturated compounds, or for the photochemical crosslinking of linear polymers,

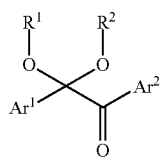

I in which
R$^1$, R$^2$, independently of one another, denote a straight-chain or branched or cyclic alkyl, cycloalkylalkyl, arylalkyl, alkenyl or cycloalkylalkenyl radical having up to 20 C atoms or an arylalkenyl radical having 8 to 20 C atoms, in each of which one or more CH$_2$ groups may be replaced by —CO—, —O— and/or —S— in such a way that no O or S atoms are adjacent and in which one or more hydrogen atoms may be replaced by halogen, or both radicals R$^1$ and R$^2$ together denote a divalent bridging group W,
W denotes a divalent radical of an aliphatic, straight-chain or branched diol having 2 to 20 C atoms,
Ar$^1$, Ar$^2$, independently of one another, denote aryl radicals which are each substituted by one or more substituents L and which may additionally be substituted by halogen, alkyl, alkoxy, each having 1 to 5 C atoms, or phenyl,
L on each occurrence, identically or differently, denotes a hydrophilic radical.

The invention furthermore relates to sealants which comprise one or more compounds selected from the group of the compounds of the formula I.

The compound I-1-1a shown below is disclosed in WO 02/48203 A1 as an intermediate for the synthesis of surface-active photoinitiators.

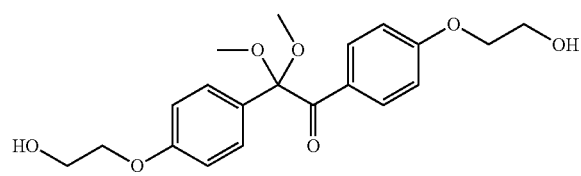

I-1-1a

The invention furthermore relates to compounds of the formula I, with the proviso that the compound of the formula I-1-1a is excluded.

A sealant in the sense of the present invention is a material which can be processed in the liquid state and which is thermally, photochemically, or thermally and photochemically curable and which, after curing, prevents the exit of liquids from an aperture.

A photopolymerisation initiator, or photoinitiator for short, in the sense of the present invention is a substance which is capable of initiating and accelerating a polymerisation under the action of actinic radiation.

Actinic radiation here and below is taken to mean electromagnetic radiation, such as near infrared, visible light, UV radiation or X-ray radiation, in particular UV radiation, and corpuscular radiation, such as electron radiation.

A resin in the sense of the present invention is a soft or highly viscous substance or substance mixture consisting of polymerisable monomers, oligomers or crosslinkable polymers which is curable by polymerisation.

A free-radical-curable resin in the sense of the present invention is a photo-polymerisable resin which contains free-radical-polymerisable functional groups, such as, for example, (meth)acrylate or allyl groups.

In the present application, all atoms also encompass their isotopes. In particular, one or more hydrogen atoms (H) may be replaced by deuterium (D), which is particularly preferred in some embodiments; a high degree of deuteration facilitates or simplifies analytical determination of compounds, in particular in the case of low concentrations.

Halogen denotes F, Cl, Br or I, preferably F or Cl.

If $R^1$ or $R^2$, called R in general below, denotes an alkyl radical, this may be straight-chain or branched. It is preferably straight-chain, has 2, 3, 4, 5, 6 or 7 C atoms and accordingly preferably denotes ethyl, n-propyl, n-butyl, n-pentyl, n-hexyl, n-heptyl, furthermore methyl, n-octyl, n-nonyl, n-decyl, n-undecyl, n-dodecyl, n-tridecyl, n-tetradecyl or n-pentadecyl.

If R denotes an alkyl radical in which one $CH_2$ group has been replaced by O, this preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6-, or 7-oxaoctyl, 2-, 3-, 4-, 5-, 6-, 7- or 8-oxanonyl, or 2-, 3-, 4-, 5-, 6-, 7-, 8- or 9-oxadecyl.

If R denotes an alkenyl radical, this may be straight-chain or branched. It is preferably straight-chain and has 2 to 10 C atoms. Accordingly, it denotes, in particular, vinyl, prop-1- or -2-enyl, n-but-1-, -2- or -3-enyl, n-pent-1-, -2-, -3- or -4-enyl, n-hex-1-, -2-, -3-, -4- or -5-enyl, n-hept-1-, -2-, -3-, -4-, -5- or -6-enyl, n-oct-1-, -2-, -3-, -4-, -5-, -6- or -7-enyl, n-non-1-, -2-, -3-, -4-, -5-, -6-, -7- or -8-enyl, or n-dec-1-, -2-, -3-, -4-, -5-, -6-, -7-, -8- or -9-enyl.

If R denotes an alkyl radical in which one $CH_2$ group has been replaced by —O— and one $CH_2$ group has been replaced by —CO—, these are preferably adjacent. This thus preferably contains an acyloxy group —CO—O— or an oxy-carbonyl group —O—CO—. These are preferably straight-chain and have 2 to 6 C atoms. Accordingly, they denote, in particular, acetyloxy, propionyloxy, butyryloxy, pentanoyloxy, hexanoyloxy, acetyloxymethyl, propionyloxy-methyl, butyryloxymethyl, pentanoyloxymethyl, 2-acetyloxyethyl, 2-propionyloxyethyl, 2-butyryloxyethyl, 2-acetyloxypropyl, 3-propionyl-oxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)-ethyl, 3-(methoxycarbonyl) propyl, 3-(ethoxycarbonyl)propyl or 4-(methoxy-carbonyl) butyl.

If R denotes an alkyl or alkenyl radical which is at least monosubstituted by halogen, this radical is preferably straight-chain and halogen is preferably F or Cl. In the case of polysubstitution, halogen is preferably F. The resultant radicals also include perfluorinated radicals. In the case of monosubstitution, the fluorine or chlorine substituent can be in any desired position, but is preferably in the ω-position.

Branched radicals R generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propyl-pentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The term aryl in the sense of the present invention denotes aromatic hydro-carbon radicals or derivatives thereof. These may be monocyclic, polycyclic or condensed, i.e. as they are (for example phenyl), substituted by other aryl radicals (for example biphenyl) or annellated (for example naphthalene). Equally, they may contain a combination of these features (for example phenylnaphthalene).

Preferred aryl radicals consist of one, two or three ring elements having 6 to 25 C atoms, which may optionally be substituted and may contain annellated aliphatic rings.

Preferred aryl radicals are derived, for example, from the compounds benzene, biphenyl, terphenyl, naphthalene, tetrahydronaphthalene, anthracene, binaphthyl, phenanthrene, 9,10-dihydrophenanthrene, pyrene, dihydropyrene, fluorene, indane, indenofluorene, spirobifluorene, etc.

The aryl radicals mentioned above and below may furthermore be substituted by alkyl, alkoxy, thioalkyl, fluorine, fluoroalkyl or further aryl groups.

The cycloalkyl radicals include both saturated and unsaturated rings, i.e. those which contain exclusively single bonds and those which contain one or more double or triple bonds, without being aromatic. Heterocycles contain one or more heteroatoms, preferably selected from S, N, O, Se and Si.

The (non-aromatic) alicyclic or heterocyclic radicals may be monocyclic, i.e. contain one ring (for example cyclohexane), or polycyclic, i.e. they contain a number of rings, such as, for example, decalin or bicyclooctane. Particular preference is given to saturated rings. Preference is furthermore given to mono-, bi- or tricyclic groups having 3 to 25 ring atoms, which may optionally be annellated and may optionally be substituted. Preference is furthermore given to 5-, 6-, 7- or 8-membered cyclic hydrocarbons in which one or more $CH_2$ groups have been replaced by Si and/or one or more CH or $CH_2$ groups have been replaced by N and/or one or more non-adjacent $CH_2$ groups have been replaced by O or S. Preferred substituents of the alicyclic radicals are alkyl or alkenyl radicals as defined above.

Preferred alicyclic and heterocyclic groups are derived, for example, from the parent structures cyclopentane, tetrahydrofuran, tetrahydrothiophene, pyrrolidine, cyclohexane, silinane, cyclohexene, tetrahydropyran, tetra-hydrothiopyran, 1,3-dioxane, 1,3-dithiane, piperidine and cycloheptane, and condensed rings, such as tetrahydronaphthalene, decalin, indane, bicyclo-[1.1.1]pentane, bicyclo[2.2.2]octane, spiro[3.3]heptane and octahydro-4,7-methanoindane.

The photoinitiator according to the invention can be used either alone or in combination with two or more compounds thereof. The photoinitiator according to the invention can be used together with one or more sensitisers and one or more further photoinitiators. The choice, combination and mixing ratio of the photopolymerisation initiator and sensitiser can be determined in a suitable manner in accordance with the ultraviolet-curing monomer and the instrument to be used.

Typical examples of further photopolymerisation initiators and sensitisers include acetophenone, 2,2-diethoxyacetophenone, p-dimethylaminoacetophenone, p-dimethylaminopropiophenone, benzophenone, 2-chlorobenzophenone, p,p'-dichlorobenzophenone, p,p'-bisdiethylaminobenzophenone, Michler's ketone, benzil, benzoin, benzoin methyl ether, benzoin ethyl ether, benzoin isopropyl ether, benzoin n-propyl ether, benzyl dimethyl ketal, tetramethylthiuram monosulfide, thioxanthone, 2-chlorothioxanthone, 2-methylthioxanthone, azobisisobutyronitrile, benzoin peroxide, di-tert-butyl peroxide, 1-hydoxycyclohexyl phenyl ketone, 2-hydroxy-2-methyl-1-phenyl-propan-1-one, 1-(4-isopropylphenyl)-2-hydroxy-2-methylpropan-1-one and methylbenzoyl formate, and the commercially available products Irgacure651®, Irgacure184®, Irgacure907®, Irgacure369® or Darocure1173® (Ciba AG).

The amount used is generally 0.1 to 10% by weight, based on the total weight of the ultraviolet-curing resin. Photopolymerisation initiators of the cationic polymerisation type which can be used are initiators such as aromatic diazonium salts, aromatic halonium salts, aromatic sulfonium salts and metallocene compounds. Specific examples thereof include triphenyl-sulfonium hexafluorophosphate, diphenyliodinium hexafluoroantimonate and the like. The monomer of the cationic polymerisation type is preferably heated within a range from 80° C. to 170° C., in particular from 100° C. to 150° C., for complete curing. The duration of the heating is generally between 5 and 30 minutes, which can vary depending on the conditions.

A hydrophilic radical in the sense of the present invention is a straight-chain or branched or cyclic alkyl radical which is substituted by one or more hydroxyl groups and/or epoxy groups and in which one or more $CH_2$ groups may be replaced by —O— or —$NR^O$— in such a way that no O atoms are adjacent, in which one or more $CH_2$ groups may be replaced by —NH— and in which one or more >CH— groups in the branches may be replaced by >N—.

Examples of typical hydrophilic radicals are the groups indicated below for L.

In a preferred embodiment, use is made of photoinitiators of the formula I in which $R^1$, $R^2$, independently of one another, denote a straight-chain or branched alkyl radical having 1 to 7 C atoms, W denotes —$(CH_2)_2$—, —$(C(CH_3)_2)_2$—, —$(CH_2)_3$— or —$CH_2C(CH_3)_2CH_2$—, $Ar^1$, $Ar^2$, independently of one another, denote 1,4-phenylene, which is in each case substituted by a substituent L, L denotes —$CH_2$-L', —O-L' or —$N(L')_2$, L' denotes a straight-chain or branched alkyl radical having 1 to 20 C atoms, in which one or more $CH_2$ groups may be replaced by cycloalkanediyl radicals having 3 to 8 ring atoms and in which one or more non-adjacent $CH_2$ groups may be replaced by O and in which one or more H atoms may be replaced by —OH or

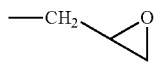

L preferably denotes —$(CH_2)_pOG$, —$O(CH_2)_{m+1}OG$, —$(CH_2)_n(OCH_2CH_2)_mOG$, —$(O)_n(CH_2)_mCH(OH)CH_2OG$, —$O(CH_2CH_2)_{m+1}OCH_2CH(OG)CH_2OG$, —$OC(CH_2OG)_3$, —$OC(CH_2OG)_2(CH_2)_nH$, —$(CH_2)_nOCH_2CH(OH)CH_2OG$, —$(OCH_2CH_2)_mOCH_2CH(OG)CH_2OG$, —$(CH_2)_nOCH_2(CH)_m((CH_2)_mOG)_2$, —$(CH_2)_nOC(CH_2OG)_3$, —$(CH_2)_mOC(CH_2OG)_2(CH_2)_nH$, —$N((CH_2)_{m+1}OG)_2$, —$N((CH_2CH_2O)_mG)_2$, —$N((CH_2)_mCH(OG)CH_2OG)_2$ or

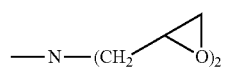

in which
m denotes an integer from 1 to 10,
n, p each, independently of one another, denote an integer from 0 to 10,
G denotes H,

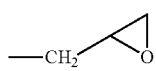

or
a monosaccharide radical selected from glucopyranose and glucofuranose, preferably glucose;
particularly preferably H, with the proviso that G cannot be H if p is equal to 0.

Particular preference is given to compounds of the formulae

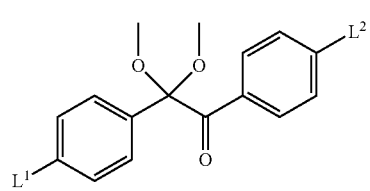
I-1

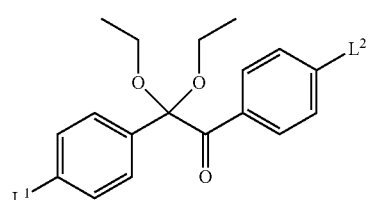
I-2

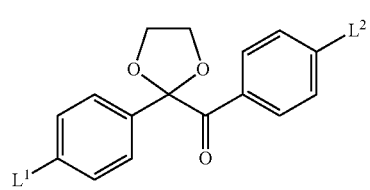
I-3

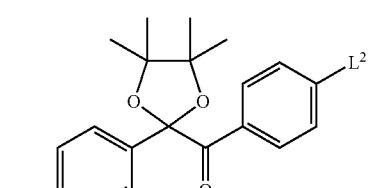
I-4

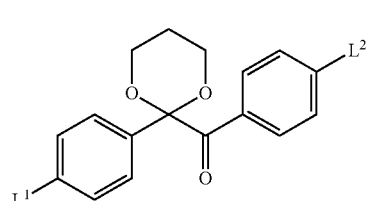
I-5

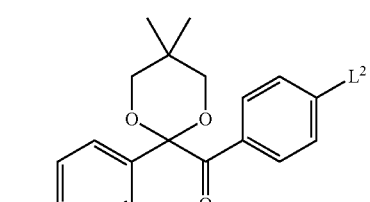
I-6

In a further preferred embodiment, the compounds of the formula I are selected from the compounds of the formula I-1. Particularly preferred sub-formulae of the formula I-1 are the sub-formulae I-1-1 to I-1-14.

I-1-1
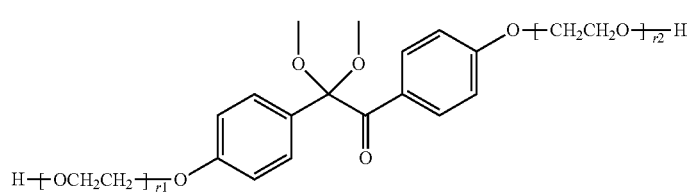
I-1-2
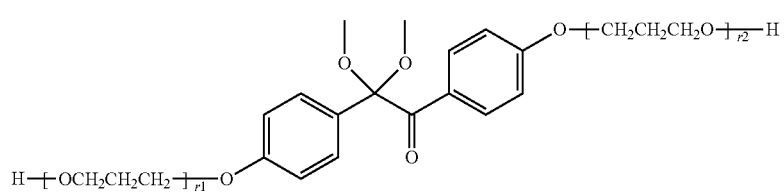
I-1-3
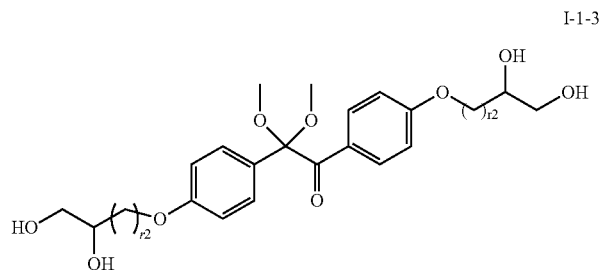
I-1-4
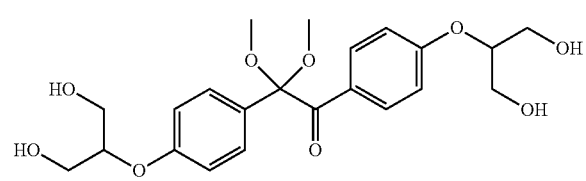
I-1-5
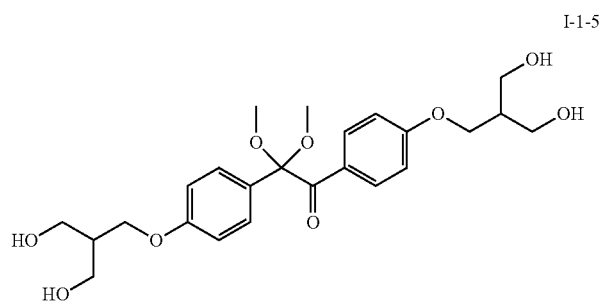
I-1-6
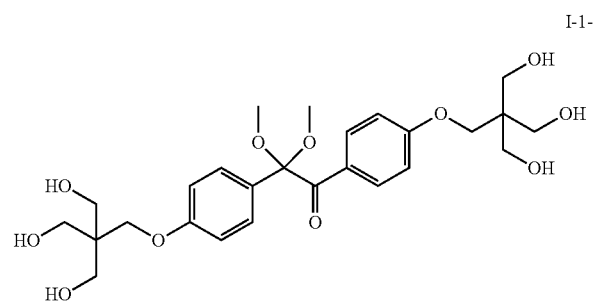
I-1-7
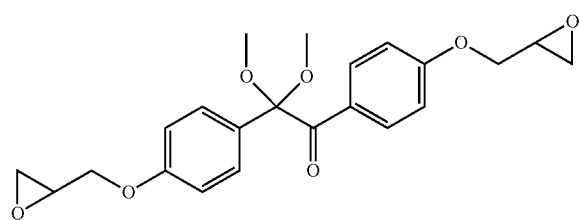
I-1-8
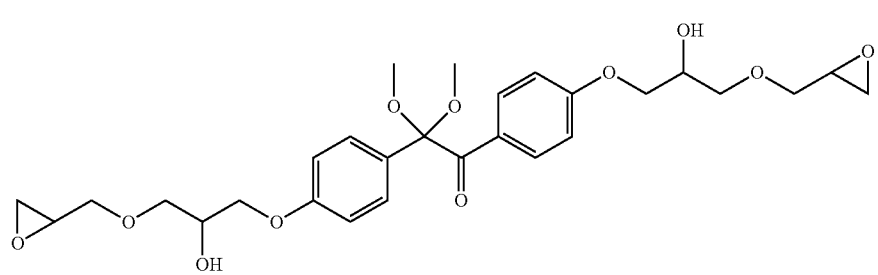

-continued

I-1-9
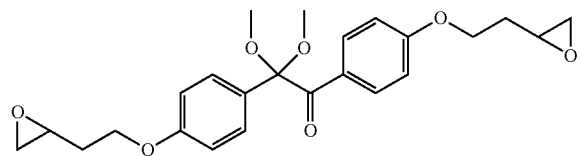

I-1-10
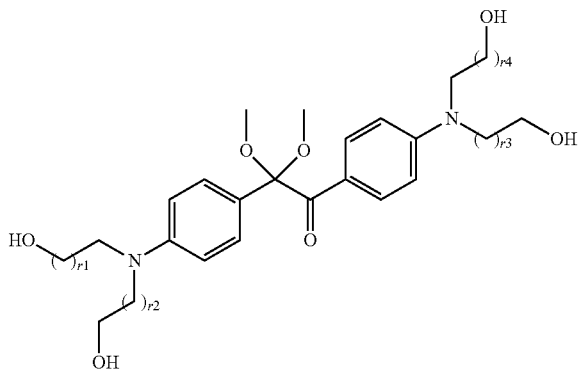

I-1-11
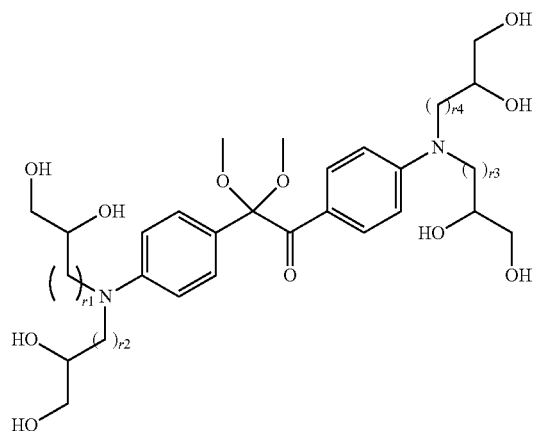

I-1-12
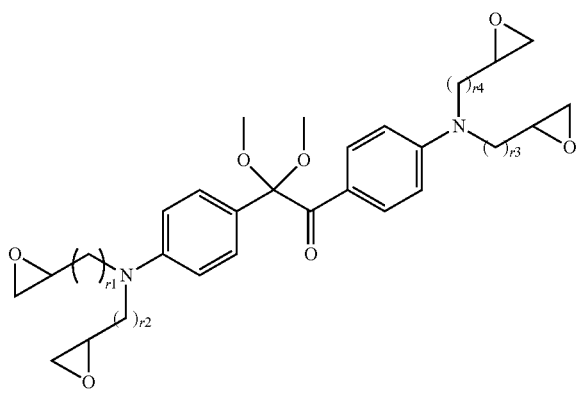

I-1-13
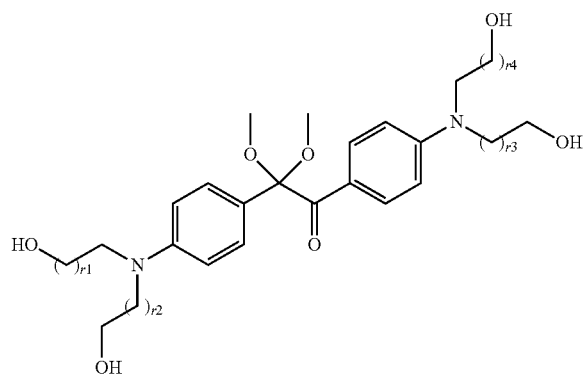

I-1-14
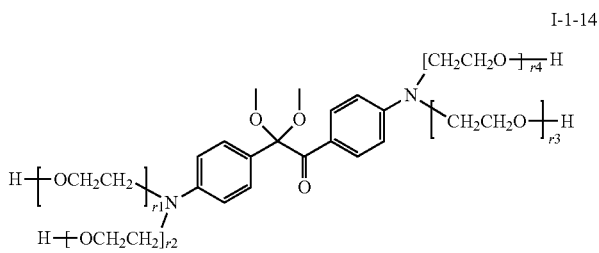

in which r1, r2, r3 and r4, independently of one another, denote 1, 2 or 3, preferably 1.

In a preferred embodiment of the present invention, use is made of compounds of the formula I whose octan-1-ol/water partition coefficient, calculated by the method of A. K. Ghose, A. Pritchett and G. M. Crippen, *J. Comput. Chem.* 1988, 9, 80-90, has a value of log P≤3.2.

Log P is preferably greater than 0.1 and less than 3.2, particularly preferably greater than 0.25 and less than 3.0, very particularly preferably greater than 0.5 and less than 2.8.

Table 1 below shows examples of particularly preferred compounds of the formula I and their calculated log P values.

TABLE 1

| No. | Structure | log P |
|---|---|---|
| 1 | 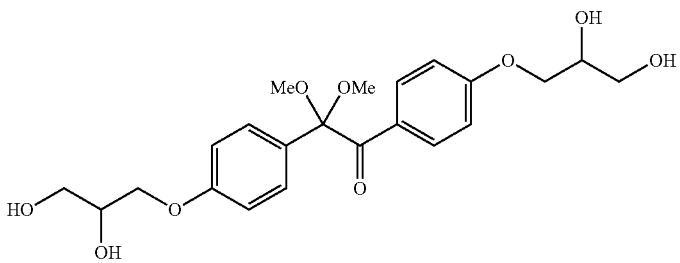 [SMILES: COC(OC)(C(=O)c1ccc(OCC(O)CO)cc1)c1ccc(OCC(O)CO)cc1] | 1.30 |
| 2 | 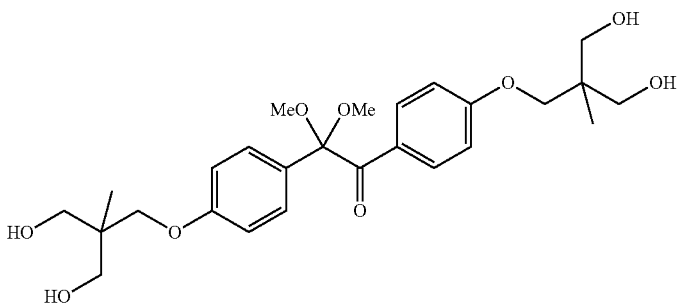 [SMILES: COC(OC)(C(=O)c1ccc(OCC(C)(CO)CO)cc1)c1ccc(OCC(C)(CO)CO)cc1] | 2.68 |
| 3 | 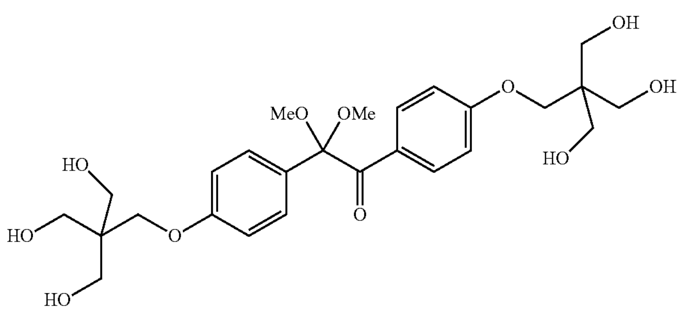 [SMILES: COC(OC)(C(=O)c1ccc(OCC(CO)(CO)CO)cc1)c1ccc(OCC(CO)(CO)CO)cc1] | 0.56 |
| 4 | 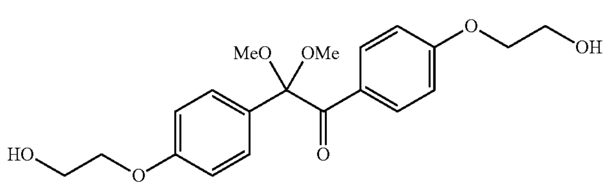 [SMILES: COC(OC)(C(=O)c1ccc(OCCO)cc1)c1ccc(OCCO)cc1] | 2.37 |
| 5 | 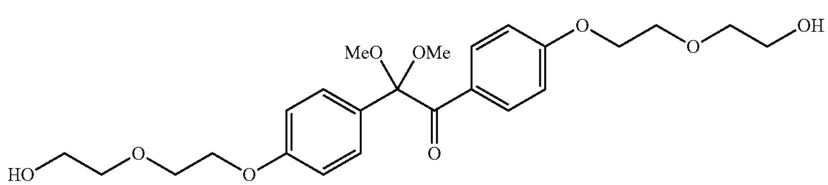 [SMILES: COC(OC)(C(=O)c1ccc(OCCOCCO)cc1)c1ccc(OCCOCCO)cc1] | 2.06 |
| 6 | 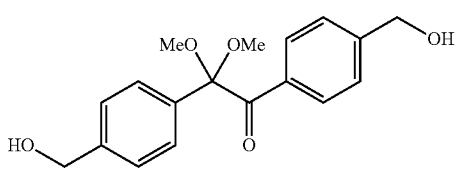 [SMILES: COC(OC)(C(=O)c1ccc(CO)cc1)c1ccc(CO)cc1] | 2.51 |

TABLE 1-continued

Examples and their log P value

| No. | Structure | log P |
|---|---|---|
| 7 | [structure] | 3.07 |
| 8 | [structure] | 2.16 |
| 9 | [structure] | 2.56 |
| 10 | [structure] | 2.55 |

In a preferred embodiment of the present invention, the compounds of the formula I are used in sealants for the production of liquid-crystal displays.

The invention furthermore relates to sealants for liquid-crystal displays which comprise one or more compounds of the formula I.

Sealants for liquid-crystal displays are known from the prior art and are disclosed, for example, in EP 1 559 735 A1, EP 2 381 304 A1, EP 1 780587A1 and EP 2 586 827 A1. The sealants according to the invention are preferably photochemically curable. The sealants according to the invention are particularly preferably both photochemically curable and thermally curable.

The sealants according to the invention preferably comprise a) one or more curable resins which comprise compounds which are each substituted by one or more epoxide groups (called "epoxides" below), and/or b) one or more compounds which are each substituted by one or more acrylate or methacrylate groups (called "(meth)acrylates" below), and/or c) one or more compounds which are substituted both by epoxide groups and by (meth)acrylate groups (called "epoxide acrylates" below).

The individual components a), b) and c) here can be in the form of both monomers and oligomers. The choice of the components is in principle not restricted to certain compounds. The polymerisable compounds are preferably di-, tri- or polyreactive, i.e. they contain two, three or more reactive epoxide and/or (meth)acrylate groups. With a view to the lowest possible contamination of the liquid crystal with the components of the sealant, preference is given to resins which contain hydroxyl groups, sulfonyl groups or ether groups.

Besides one or more compounds of the formula I, the sealants according to the invention preferably comprise i) a free-radical-curable resin,
ii) an epoxy resin,
iii) an epoxy curing agent.

Examples of free-radical-curable resins are (meth)acrylates and unsaturated polyester resins, which can each be used alone or in a mixture of one or more such substances. The monomeric (meth)acrylates preferably contain two or more (meth)acrylate groups per molecule.

Examples of (meth)acrylates are urethane (meth)acrylates containing a urethane bridge and epoxy (meth)acrylates which carry one or more glycidyl groups besides one or more (meth)acrylate groups.

Examples of urethane (meth)acrylates are compounds which are obtained by reaction between diisocyanates (for example isophorone diisocyanate) and compounds which are able to add onto isocyanates, such as, for example, acrylic acid or hydroxyethyl acrylate.

These derivatives may contain chain extensions by caprolactone or polyols and are commercially available, for example, under the trade names U-122P, U-3, 40P, U-4HA and U-1084A (Shin-Nakamura Chemical), and KRM 7595, KRM 7610 and KRM 7619 (Daicel Cytec Co.).

Examples of epoxy (meth)acrylates are derivatives of epoxy resins (for example bisphenol A epoxy resins or propylene glycol diglycidyl ether) and (meth)acrylic acid and are commercially available, for example, under the trade names EA-1020, EA-6320 and EA-5520 (Shin-Nakamura Chemical), and EPDXY ESTER 70PA and EPDXY ESTER 3002A (Kyoiesha Chemical). Further examples of suitable (meth)acrylates are methyl methacrylate, tetrahydrofurfuryl methacrylate, benzyl methacrylate, isobornyl methacrylate, 2-hydroxyethyl methacrylate, glycidyl methacrylate, (poly) ethylene glycol dimethacrylate, 1,4-butanediol dimethacrylate, 1,6-hexanediol dimethacrylate, trimethylolpropane triacrylate, pentaerythritol triacrylate and glycerol dimethacrylate.

The group of free-radical-curable resins likewise includes epoxide acrylates which contain one or more (meth)acrylate groups and one or more epoxide groups per molecule and which are prepared by partially reacting the epoxy resins described above with (meth)acrylic acid in the presence of a base; they furthermore include compounds which are prepared by reacting bi- or polyfunctional isocyanates with half an equivalent of a hydroxyl-containing (meth)acrylate and subsequently with half an equivalent of glycidol; they furthermore include compounds which are prepared by reacting a methacrylate which is substituted by an isocyanate group with glycidol.

Such materials are available, for example, under the trade names UVAC 1561 (Daicel Cytec) and 4HBAGE (Nippon Kasei).

Examples of latent epoxide curing agents in accordance with the present invention are dicyandiamides, modified polyamines, hydrazides, 4,4'-diaminodiphenyl sulfone, boron trifluoride/amine complexes, as well as imidazole, guanidine, urea, melamine and derivatives thereof. Examples of modified polyamines are epoxy adducts of polyamines, amides of polyamines and Mannich-modified polyamines. Examples of polyamines are aliphatic polyamines, such as, for example, ethylenediamine, diethylenetriamine, triethylenetetramine, tetraethylene-pentamine, 1,2-diaminopropane, polyoxypropylenediamine and polyoxy-propylenetriamine; alicyclic polyamines, such as, for example, isophorone-diamine, menthenediamine, bis(4-amino-3-methyldicyclohexyl)methane, diaminodicyclohexylmethane, bis(aminomethyl)cyclohexane, N-aminoethyl-piperazine and 3,9-bis(3-aminopropyl)-2,4,8,10-tetraoxaspiro[5.5]undecane; aromatic polyamines, such as, for example, m-phenylenediamine, p-phenylenediamine, tolylene-2,4-diamine, tolylene-2,6-diamine, mesitylene-2,4-diamine, mesitylene-2,6-diamine, 3,5-diethyltolylene-2,4-diamine and 3,5-diethyltolylene-2,6-diamine, biphenylene-diamine, 4,4-diaminodiphenyl-methane, 2,5-naphthylenediamine and 2,6-naphthylenediamine; and imidazoles, such as, for example, 2-methylimidazole, 2-ethyl-4-methylimidazole, 2-isopropylimidazole, 2-undecylimidazole, 2-heptadecyl-imidazole, 2-phenylimidazole, 2-phenyl-4-methylimidazole and 2-amino-propylimidazole.

The epoxy adducts are prepared by the addition, which is familiar to the person skilled in the art, of epoxides onto polyamines. The epoxides are preferably aliphatic compounds, aromatic compounds, etc. These compounds can each be employed alone or in a mixture with other epoxides.

Examples of alicyclic epoxides are polyglycidyl ethers of polyols containing at least one alicycle, cyclohexene oxide or cyclopentene oxide and derivatives thereof, in particular saturated derivatives of bisphenol A diglycidyl ether, 3,4-epoxycyclohexylmethyl 3,4-epoxycyclohexanecarboxylate, 3,4-epoxy-1-methylcyclohexyl 3,4-epoxy-1-methylcyclohexanecarboxylate, 6-methyl-3,4-epoxycyclohexylmethyl 6-methyl-3,4-epoxycyclohexanecarboxylate, 3,4-epoxy-3-methylcyclohexylmethyl 3,4-epoxy-3-methylcyclohexanecarboxylate, 3,4-epoxy-5-methylcylcohexylmethyl 3,4-epoxy-5-methylcyclohexanecarboxylate, 2-(3,4-epoxycyclohexyl-5,5-spiro-3,4-epoxy) cyclohexanemetadioxane, bis(3,4-epoxycyclohexylmethyl) adipate, 3,4-epoxy-6-methylcyclohexyl carboxylate, methylenebis(3,4-epoxycyclohexane), dicyclopentadiene diepoxide, ethylene bis(3,4-epoxycyclohexanecarboxylate), dioctyl epoxyhexahydrophthalate and di-2-ethylhexyl epoxyhexahydrophthalate.

Commercially available products which contain such compounds are, for example, UVR-6100, UVR-6105, UVR-6110, UVR-6128 and UVR-6200 (Union Carbide); Celloxide 2021, Celloxide 2021P, Celloxide 2081, Celloxide 2083, Celloxide 2085, Celloxide 2000, Celloxide 3000, Cyclomer A200, Cyclomer M100, Cyclomer M101, Epolead GT-301, Epolead GT-302, Epolead 401, Epolead 403, ETHB and Epolead HD300 (Daicel Chemical Industries, Ltd.) and KRM-2110 and KRM-2199 (ADEKA Corp.).

Examples of aromatic epoxides are polyglycidyl ethers of polyhydric phenols or alkylene oxide adducts thereof which contain at least one aromatic ring, such as, for example, glycidyl ethers of bisphenol A, bisphenol F, or alkylene oxides thereof, as well as epoxy-novolak resins.

Examples of aliphatic epoxides are polyglycidyl ethers of aliphatic polyols or alkylene oxide adducts thereof, polyglycidyl esters of aliphatic long-chain polycarboxylic acids, glycidyl poly(meth) acrylates, in particular 1,4-butanediol diglycidyl ether, 1,6-hexanediol diglycidyl ether, glycerol triglycidyl ether, trimethylolpropane triglycidyl ether, sorbitol tetraglycidyl ether, dipentaerythritol hexaglycidyl ether, polyethylene glycol diglycidyl ether and polypropylene glycol diglycidyl ether; polyglycidyl ethers of polyetherpolyols, prepared by addition of one or more alkylene oxides onto aliphatic polyols, such as, for example, propylene glycol, trimethylolpropane and glycerol; and diglycidyl esters of long-chain aliphatic dicarboxylic acids. Preference is furthermore given to monoglycidyl ethers of higher aliphatic alcohols, monoglycidyl ethers of phenol, cresol, butylphenol or polyether alcohols prepared by addition of alkylene oxides onto these phenols, glycidyl esters of higher fatty acids, epoxidised soybean oil, octyl epoxystearate, butyl epoxystearate and epoxidised polybutadiene.

Examples of commercially available aromatic or aliphatic epoxides are Epikote 801 and Epikote 828 (Yuka Shell Epoxy Co., Ltd.); PY-306, 0163 and DY-022 (Ciba Specialty Chemicals); KRM-2720, EP-3300, EP-4000, EP-4901, EP-4010, EP-4080, EP-4900, ED-505 and ED-506 (ADEKA); Epolite M-1230, Epolite EHDG-L, Epolite 40E, Epolite 100E, Epolite 200E, Epolite 400E, Epolite 70P, Epolite 200P, Epolite 400P, Epolite 1500NP, Epolite 1600, Epolite 80MF, Epolite 100MF, Epolite 4000, Epolite 3002 and Epolite FR-1500 (Kyoeisha Chemical); Santoto ST0000, YD-716, YH-300, PG-202, PG-207, YD-172 and YDPN638 (Tohto Kasei Co., Ltd.); TEPIC-S (Nissan Chemical Industries, Ltd.); and Epichlon N-665, Epichlon N-740, Epichlon HP-7200 and Epichlon HP-4032 (DIC Corp.).

Polyamides are obtained in a manner known to the person skilled in the art by reaction of polyamines with carboxylic acids, such as, for example, adipic acid, sebacic acid, phthalic acid or isophthalic acid.

Mannich-modified polyamines are prepared by reacting a polyamine with aldehydes, for example formaldehyde, and phenols, such as, for example, phenol, cresol, xylenol, t-butylphenol or resorcinol.

Examples of hydrazides are oxalic dihydrazide, malonic dihydrazide, succinic dihydrazide, glutaric dihydrazide, adipic dihydrazide, suberic dihydrazide, azelaic dihydrazide, sebacic dihydrazide and phthalic dihydrazide.

Examples of urea derivatives are 3-(3,4-dichlorophenyl)-1,1-dimethylurea, isophorone diisocyanate dimethylurea and tolylene diisocyanate dimethylurea.

Examples of epoxy resins (iii) are polyglycidyl ethers of polyhydric phenols, such as, for example, hydroquinone, resorcinol, pyrocatechol and phloroglucinol; polyglycidyl ethers of condensed aromatic hydroxyl compounds, such as naphthol, biphenylol, methylenebisphenol (bisphenol F), methylenebis(orthocresol), ethylidenebisphenol, isopropylidenebisphenol (bisphenol A), 4,4'-dihydroxybenzophenone, isopropylidenebis(orthocresol), tetrabromobisphenol A, 1,3-bis(4-hydroxycumylbenzene), 1,4-bis(4-hydroxycumylbenzene), 1,1,3-tris(4-hydroxyphenyl)butane, 1,1,2,2-tetra(4-hydroxyphenyl)ethane, thiobisphenol, sulfobisphenol, oxybisphenol, phenol novolak, orthocresol novolak, ethylphenol novolak, butylphenol novolak, octylphenol novolak, resorcinoil novolak and terpenediphenol; furthermore polyglycidyl ethers of polyhydric alcohols, such as ethylene glycol, propylene glycol, butylene glycol, hexanediol, polyglycol, thiodiglycol, glycerol, trimethylolpropane, pentaerythritol, sorbitol and bisphenol A/ethylene oxide adducts; homo- or copolymers of glycidyl esters of aliphatic, aromatic or alicyclic polybasic carboxylic acids, such as, for example, maleic acid, fumaric acid, itaconic acid, succinic acid, glutaric acid, suberic acid, adipic acid, azelaic acid, sebacic acid, phthalic acid, isophthalic acid, terephthalic acid, trimellitic acid, pyromellitic acid, tetrahydrophthalic acid, hexahydrophthalic acid and endo-methylenetetrahydrophthalic acid, or glycidyl methacrylate; furthermore epoxides containing a glycidylamino group, such as, for example, N,N-glycidylaniline, bis(4-(N-methyl-N-glycidylamino)phenyl)methane and diglycidyl-o-toluidine; epoxidised cycloalkenes, such as, for example, vinylcyclohexene diepoxide, dicyclopentadiene diepoxide, 3,4-epoxycyclohexylmethyl 3,4-epoxycyclohexanecarboxylate, 3,4-epoxy-6-methylcyclohexylmethyl 6-methylcyclohexanecarboxylae and bis(3,4-epoxy-6-methylcyclohexylmethyl) adipate; epoxidised conjugated polyenes, such as, for example, epoxidised polybutadiene, epoxidised acrylonitrile-butadiene copolymer and an epoxidised styrene-butadiene copolymer; furthermore heterocyclic compounds, such as triglycidyl isocyanurate.

In a preferred embodiment, the sealants according to the invention comprise further components, such as, for example, inorganic fillers, or silanes for improving the adhesive strength and the water-repellent properties, organic solvents, pigments, antifoams, conductive additives, levelling agents, etc.

The sealants according to the invention are prepared, for example, by mixing and dissolving predetermined amounts of the components employed for photocuring, the components employed for thermal curing, and, if necessary, various additives and subsequently homogenising the mixture using a known mixing device, for example a triple-roll mill, a sand mill or a ball mill.

The sealant according to the invention is suitable for sealing containers in order to prevent the exit of liquids or liquid crystals, in particular for sealing liquid-crystal displays and very particularly for sealing liquid-crystal displays produced by the ODF process. The liquids or liquid crystals are not restricted in any way. The sealant is furthermore suitable for use in organic light-emitting diodes, organic solar cells, organic dye-sensitised solar cells and similar components.

The sealant is particularly suitable for sealing liquid-crystal displays which contain liquid crystals having polymerisable components (reactive mesogens) and/or individual liquid-crystal substances containing unsaturated groups, such as, for example, alkenyl radicals or cyclohexene-1,4-diyl units. The reactive mesogens preferably contain one or more (meth)-acrylate groups.

The invention furthermore relates to liquid-crystal displays produced using the sealant according to the invention by the ODF process.

For the production of the liquid-crystal display, spacers are added to the sealant in order to produce a precisely defined separation of the substrates and thus a precisely defined cell gap of the display, typically 2-8 µm, depending on the application. Firstly, the sealant is applied to one of the two glass substrates, followed by the amount of liquid crystal corresponding precisely to the internal volume of the finished liquid-crystal display. After the two substrates have been combined, the display is irradiated with a dose of 1000 mJ to 18,000 mJ of UV light, during which the two substrates are pressed together. The sealant is then thermally cured at 110° C. to 140° C. for 1 to 3 h.

The compounds of the general formula I can be prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants which are known per se, but are not mentioned here in greater detail.

The starting materials can, if desired, also be formed in situ by not isolating them from the reaction mixture, but instead immediately converting them further into the compounds of the general formula I.

The syntheses of compounds of the general formula I according to the invention are described by way of example in the examples. The starting substances can be obtained by generally accessible literature procedures or are commercially available.

Particularly suitable synthetic routes to the compounds according to the invention are explained below with reference to Schemes 1-4.

The synthesis of the skeleton of the compounds according to the invention, i.e. the monoketals of benzil, is carried out, for example, by the method of R. K. Summerbell, D. R. Berger, J. Amer. Chem. Soc. 1959, 81, 633-639, by oxidation of benzil ketals, as illustrated in Scheme 1 for the example of the ethylene ketal.

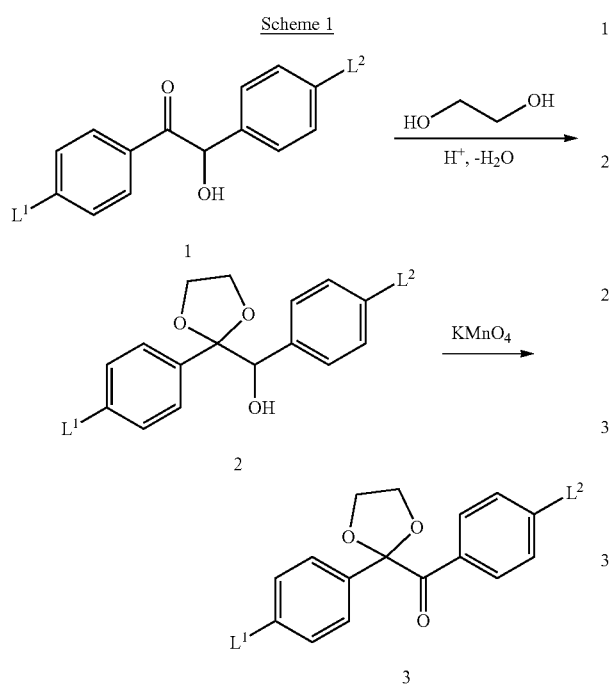

Access to dimethyl ketals (5) under basic conditions by reaction with methyl iodide in the presence of silver oxide or barium oxide in dimethylformamide is described in R. Kuhn, H. Trischmann, Chem. Ber. 1961, 94, 2258-2263 (Scheme 2).

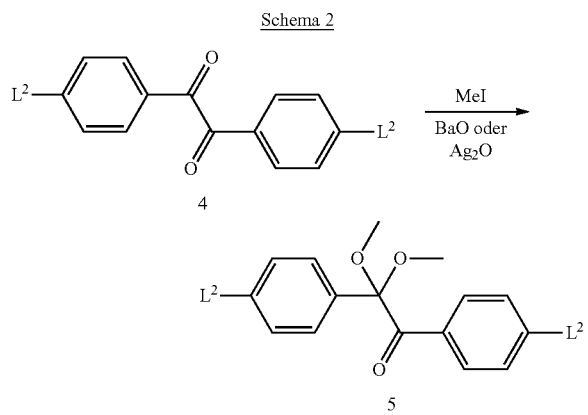

Further access to benzil monoketals is given by reaction of benzil with alcohols in the presence of thionyl chloride, as shown in Scheme 3. Scheme 3 also shows an illustrative modification of a preferred, commercially available starting material (dihydroxybenzil, 6) for the synthesis of the compounds according to the invention.

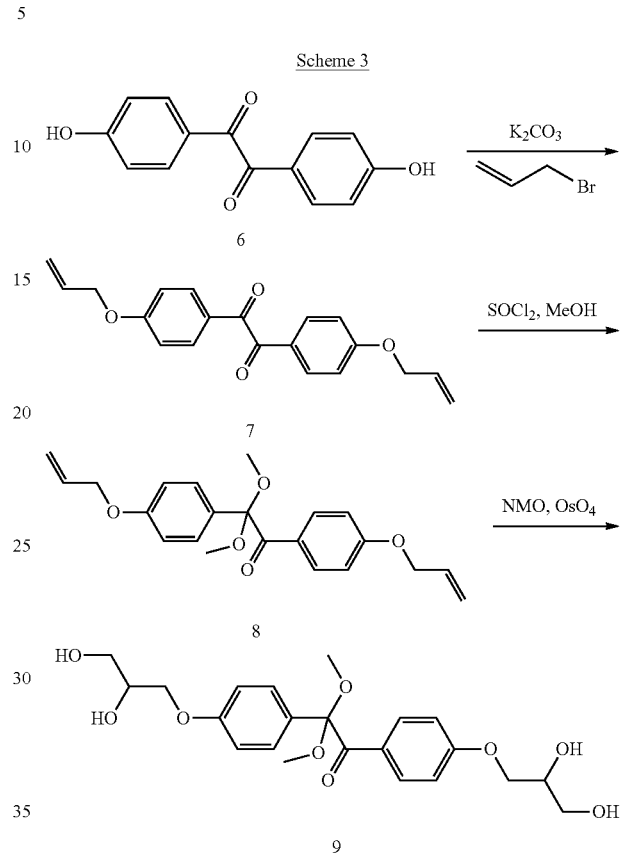

Diaminobenzil (10), which is suitable as precursor for the amine derivatives according to the invention, is disclosed in US 2005266255. This can be reacted with glycidol, for example by the method of M. F. Sorokin, *Izvestiya Vysshikh Uchebnykh Zavedenii, Khimiya i Khimicheskaya Tekhnologiya* 1982, 25, 355-360, to give compound 11 (Scheme 4).

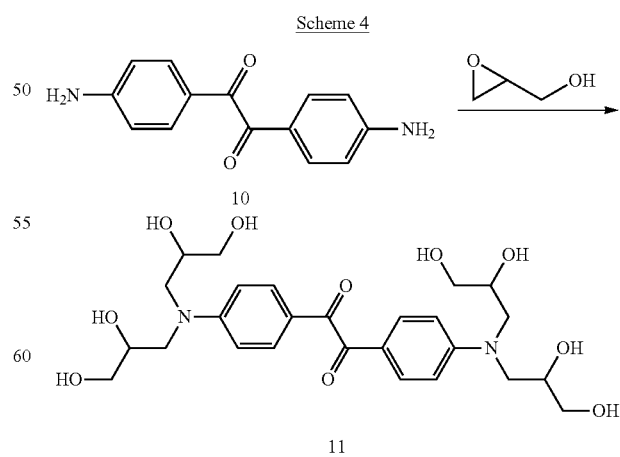

The invention likewise relates to liquid-crystal displays which have been produced using the sealants according to the invention. In a preferred embodiment, the liquid-crystal displays according to the invention are produced by the ODF process.

The liquid-crystal displays according to the invention are preferably PS-VA, PS-IPS, PS-FFS, PS-OCB or PS-TN displays.

EXAMPLES

The present invention is described in detail by the following, non-restrictive examples.

Example 1: 1,2-Bis[4-(2,3-dihydroxypropoxy)phenyl]-2,2-dimethoxyethanone 1.1 4,4'-Bis(allyloxy)benzil

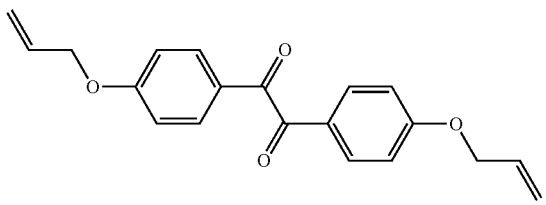 [SMILES: C=CCOc1ccc(C(=O)C(=O)c2ccc(OCC=C)cc2)cc1]

A solution of allyl bromide (23.0 g, 190 mmol) in 50 ml of dimethylformamide is added dropwise to a suspension of 4,4'-dihydroxybenzil (16.8 g, 69.4 mmol) and potassium carbonate (21.1 g, 153 mmol) in 250 ml of dimethylformamide. The batch is left to stir overnight at 80° C., added to water and extracted with dichloromethane. The combined org. phases are washed with water, dried over sodium sulfate and evaporated in vacuo. The residue is chromatographed on silica gel with dichloromethane, giving 4,4'-bis(allyloxy)benzil as a yellowish solid.

1.2 1,2-Bis(4-allyloxyphenyl)-2,2-dimethoxyethanone

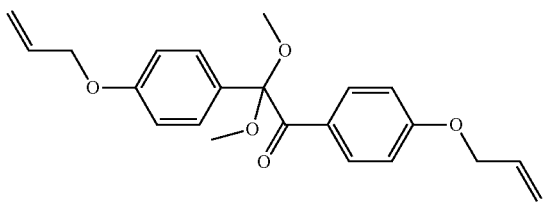 [SMILES: C=CCOc1ccc(C(=O)C(OC)(OC)c2ccc(OCC=C)cc2)cc1]

60 ml of methanol are slowly added dropwise to a suspension of 4,4'-bis-(allyloxy)benzil (17.7 g, 55.0 mmol) and thionyl chloride (53.0 ml, 0.740 mol) at such a rate that the temperature is 5-10° C. When the addition is complete, the batch is heated at 50° C. for 6 h, carefully neutralised by addition of dil. sodium hydroxide solution and extracted with ethyl acetate. The combined org. phases are washed with water and dried over sodium sulfate. The solvent is removed in vacuo, and the residue is purified by chromatography on silica gel with dichloromethane/ethyl acetate (9:1), giving 1,2-bis(4-allyloxyphenyl)-2,2-dimethoxyethanone as a yellowish oil.

1.3 1,2-Bis[4-(2,3-dihydroxypropoxy)phenyl]-2,2-dimethoxyethanone

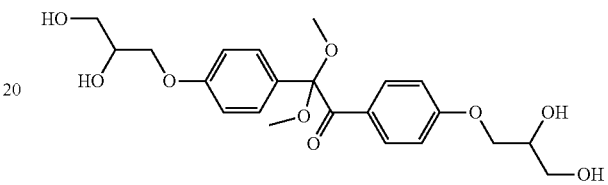

6.4 ml of a 4 percent aqueous osmium tetraoxide solution are added dropwise to a solution of 1,2-bis(4-allyloxyphenyl)-2,2-dimethoxyethanone (7.6 g) and 4-methylmorpholine N-oxide (8.2 g) in 90 ml of acetone and 20 ml of water at such a rate that the temperature does not exceed 20° C. After stirring overnight, 0.6 g of sodium metabisulfite are added, and the batch is left to stir for 1 h. The solution is extracted with ethyl acetate, and the combined org. phases are purified by chromatography on silica gel with dichloromethane/methanol (9:1), giving 1,2-bis[4-(2,3-dihydroxypropoxy)-phenyl]-2,2-dimethoxyethanone as a wax-like solid.

$^1$H-NMR (d$_6$-DMSO, 500 MHz, with TFA exchange)

δ=7.79 ppm (d., 4H, Ar—H), 7.79 (d., 4H, Ar—H), 4.06-3.82 (br. m., 8H, 4×CH$_2$O), 3.45 (br. m., 2H, 2×CH$_2$CHOHCH$_2$), 3.14 (s., 6H, 2×OCH$_3$).

Use Example

A nematic liquid-crystal mixture M-1 is prepared as follows:

| Mixture M-1 Composition | | |
|---|---|---|
| | Compound | Concentration/ |
| No. | Structural formula | % by weight |
| 1 | | 9.50 |
| 2 | | 5.00 |

-continued
| | Mixture M-1 Composition | |
|---|---|---|
| | Compound | Concentration/ |
| No. | Structural formula | % by weight |
| 3 | 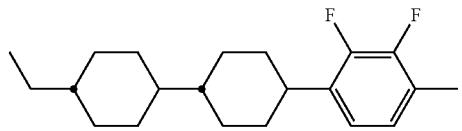 | 9.50 |
| 4 | 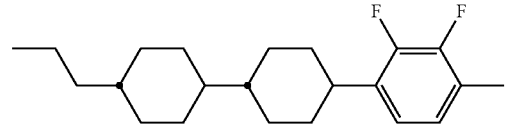 | 10.50 |
| 5 | 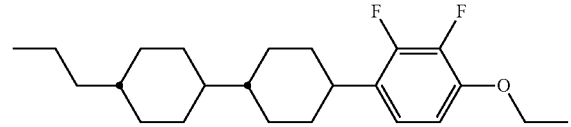 | 10.50 |
| 6 | 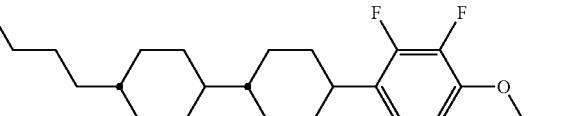 | 9.50 |
| 7 | 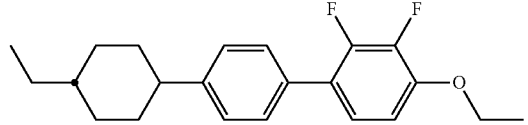 | 12.00 |
| 8 | 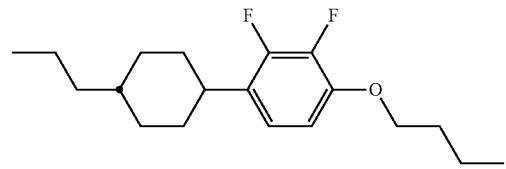 | 9.00 |
| 9 | 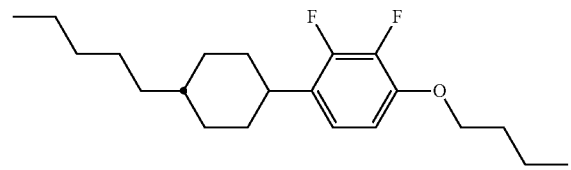 | 11.00 |
| 10 | 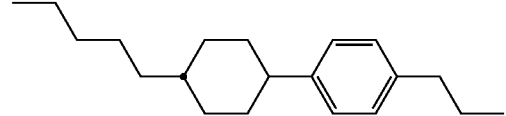 | 13.50 |
| Σ | | 100.00 |

A polymerisable liquid-crystal mixture P-1 consisting of 1. 99.7% by weight of the nematic liquid-crystal mixture M-1 and
2. 0.3% by weight of the polymerisable compound RM-1

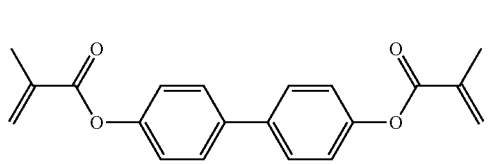

RM-1 is prepared. Three samples of in each case 0.5 g of mixture P-1 are stored together with in each case 1 g of the commercially available sealant Unocol 2094® (APM Technica GmbH, Pürgen-Ummendorf), the latter in each case containing 1. no photoinitiator
2. 3.0% by weight of the photoinitiator according to the invention from Example 1
3. 3.0% by weight of the commercially available photoinitiator Irgacure651® of the structure shown below in a tightly sealed vial at 80° C. for 7 d with exclusion of air and light. A fourth sample of mixture P-1 is stored under the same conditions without the presence of sealant (blank experiment).

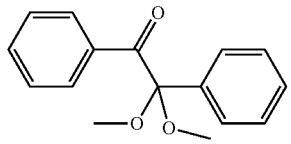

Irgacure 651®

TABLE 2

| Ex. | Mixture | Sealant | Photoinitiator | Initiator concentration |
|---|---|---|---|---|
| 0.1 (blank experiment) | P-1 | — | — | — |
| 0.2 (comparison) | P-1 | Unocol 2094® | — | — |
| 1 | P-1 | Unocol 2094® | Irgacure651® | 3.0% by weight |
| 2 | P-1 | Unocol 2094® | Ex. 1 | 3.0% by weight |

The mixtures are subsequently separated off from the sealant, in each case divided into two parts, introduced into PS-VA test cells and irradiated with a metal halide UV lamp with an intensity of 100 mW/cm² at 40° C. for a duration of 60 s or 180 s.

The PS-VA test cells consist of two plane-parallel glass plates having a cell gap of 4 μm, each of which are coated with an ITO electrode and with a polyimide alignment layer on top.

After the irradiation, the concentration of the polymerisable compound RM-1 is determined by HPLC. The results are shown in Table 3.

TABLE 3

| Ex. | Concentration of RM/rel % after | | |
|---|---|---|---|
| | t = 0 s | t = 60 s | t = 180 s |
| 0.1 (blank experiment) | 100 | 88 | 56 |
| 0.2 (comparison) | 70 | 64 | 51 |
| 1 | 71 | 66 | 51 |
| 2 | 72 | 0 | 0 |

As can be seen from Table 3, approximately the same amount of the polymerisable compound RM-1 (70-72%) can be detected in the samples from Examples 0.2, 1 and 2 after the storage test. In the blank experiment (Ex. 0.1, without sealant), somewhat more RM-1 is detectable (relative 100%), which indicates dissolution of the RM out of the liquid crystal by the sealant or slow decomposition of RM-1 by components of the sealant in the other three samples during the storage test. As is furthermore evident, the presence of Irgacure651® during the storage test subsequently results in rapid polymerisation of RM-1 on UV irradiation of the liquid-crystal mixture; RM-1 is no longer detectable after only 60 s, which suggests that considerable amounts of photoinitiator have dissolved in the liquid-crystal mixture (Ex. 2).

The decrease in the RM concentration in the Examples 0.1 and 0.2 is due to the, albeit slight, reactivity of RM-1, which polymerises slowly even without photoinitiator.

As can be seen, the decrease in the concentration of RM-1 after contact of mixture P-1 with sealant comprising the photoinitiator according to the invention (Example 1) is comparable with the sample from Example 0.2 (without photoinitiator), which suggests that no photoinitiator according to the invention has been dissolved out of the sealant in the liquid crystal during the storage test, which means that the photoinitiator according to the invention is eminently suitable for the production of liquid-crystal displays, in particular if undesired reactions during curing of sealants during production are to be avoided.

The invention claimed is:

1. A photopolymerization or crosslinking process sealing a liquid crystalline display, comprising sealing said liquid crystalline display by photopolymerization of polymerizable substance mixtures which comprise unsaturated compounds, or photochemical crosslinking of linear polymers, by subjecting said unsaturated compounds or linear polymers in said display to photopolymerization or crosslinking conditions respectively in the presence of an initiator of formula I

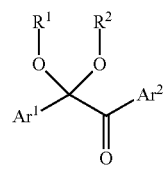

I in which

R¹, R², independently of one another, denote a straight-chain or branched or cyclic alkyl, cycloalkylalkyl, arylalkyl, alkenyl or cycloalkylalkenyl radical having up to 20 C atoms or an arylalkenyl radical having 8 to 20 C atoms, in each of which one or more CH₂ groups may be replaced by —CO—, —O— and/or —S— in such a way that no O or S atoms are adjacent and in which one or more hydrogen atoms may be replaced by halogen, or both radicals R¹ and R² together denote a divalent bridging group W, W denotes a divalent radical of an aliphatic, straight-chain or branched diol having 2 to 20 C atoms, Ar¹, Ar², independently of one another, denote aryl radicals which are each substituted by one or more substituents L and which may additionally be substituted by halogen, alkyl, alkoxy, each having 1 to 5 C atoms, or phenyl, L on each occurrence, identically or differently, denotes a hydrophilic radical.

2. The process according to claim 1, wherein, in formula I,

R¹, R², independently of one another, denote a straight-chain or branched alkyl radical having 1 to 7 C atoms, Ar¹, Ar², independently of one another, denote 1,4-phenylene, which is in each case substituted by a substituent L, L denotes —CH₂-L', —O-L' or —N(L')₂, L' denotes a straight-chain or branched alkyl radical having 1 to 19 C atoms, in which one or more CH₂ groups may be replaced by cycloalkanediyl radicals having 3 to 8 ring atoms and in which one or more non-adjacent CH₂ groups may be replaced by O and in which one or more H atoms may be replaced by —OH or

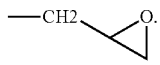

3. The process according to claim 1, wherein, in formula I, R¹, R² denote W,

W denotes a divalent radical of an aliphatic, straight-chain or branched diol having 2 to 10 C atoms, Ar¹, Ar², independently of one another, denote 1,4-phenylene, which is in each case substituted by a substituent L, L denotes —CH₂-L', —O-L' or —N(L')₂, L' denotes a straight-chain or branched alkyl radical having 1 to 19 C atoms, in which one or more CH₂ groups may be replaced by cycloalkanediyl radicals having 3 to 8 ring atoms and in which one or more non-adjacent CH₂ groups may be replaced by O and in which one or more H atoms may be replaced by —OH or

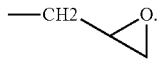

4. The process according claim 1, wherein the compounds of the formula I are compounds of the following subformulae:

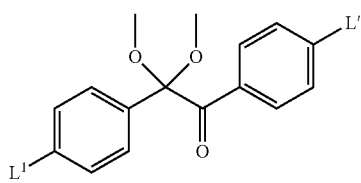

I-1

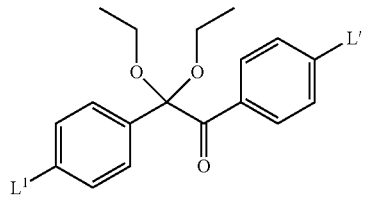

I-2

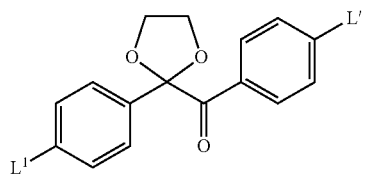

I-3

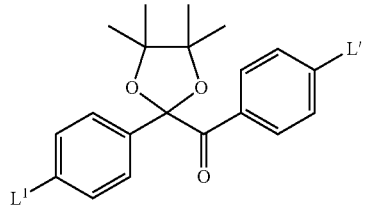

I-4

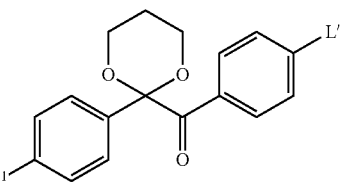

I-5 or

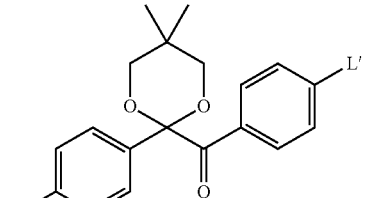

I-6 where

L denotes —CH₂-L', —O-L' or —N(L')₂,

L' denotes a straight-chain or branched alkyl radical having 1 to 19 C atoms, in which one or more CH₂ groups may be replaced by cycloalkanediyl radicals having 3 to 8 ring atoms and in which one or more non-adjacent CH₂ groups may be replaced by O and in which one or more H atoms may be replaced by -OH or

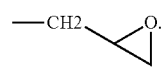

5. The process according to claim 1, wherein

L denotes —(CH₂)$_p$OG, —O(CH₂)$_{m+1}$OG, —(CH₂)$_n$(OCH₂CH₂)$_m$OG, —(O)$_n$(CH₂)$_m$CH(OH)CH₂OG, —O(CH₂CH₂)$_{m+1}$OCH₂CH(OG), CH₂OG, —OC(CH₂OG)₃, —OC(CH₂OG)₂(CH₂)$_n$H, —(CH₂)$_n$OCH₂CH(OH)CH₂OG, —(OCH₂CH₂)$_m$OCH₂CH(OG)CH₂OG, —(CH₂)$_n$OC-H₂(CH)$_m$((CH₂)$_m$OG)₂, —(CH₂)$_n$OC(CH₂OG)₃, —(CH2)$_m$OC $(CH_2OG)_2(CH_2)_nH$,    $-N((CH_2)_{m+1}OG)_2$,
$-N((CH_2CH_2O)_mG)_2$,    $-N((CH_2)_mCH(OG)CH_2OG)_2$ or

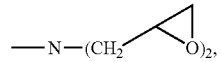

m denotes an integer from 1 to 10,
n, p denote an integer from 0 to 10,
G denotes H,

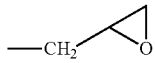

or a monosaccharide radical selected from glucopyranose and glucofuranose, with the proviso that G cannot be H if p is equal to 0.

6. The process according to claim 1, wherein the compounds of the formula I have an octan-1-ol/water partition coefficient of logP ≤3.2.

7. A liquid-crystal display, containing in said liquid-crystal display a sealant comprising a) one or more curable epoxide resins which comprise compounds which are each substituted by one or more epoxide groups and/or b) one or more (meth) acrylate compounds which are each substituted by one or more acrylate or meth-acrylate groups and/or c) one or more epoxide acrylate compounds which are substituted both by epoxide groups and by (meth)acrylate groups and d) a compound of the formula I

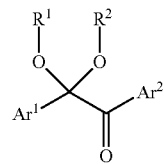

in which
R¹, R², independently of one another, denote a straight-chain or branched or cyclic alkyl, cycloalkylalkyl, arylalkyl, alkenyl or cycloalkylalkenyl radical having up to 20 C atoms or an arylalkenyl radical having 8 to 20 C atoms, in each of which one or more $CH_2$ groups may be replaced by —CO—, —O— and/or —S— in such a way that no O or S atoms are adjacent and in which one or more hydrogen atoms may be replaced by halogen, or both radicals R¹ and R² together denote a divalent bridging group W,
W denotes a divalent radical of an aliphatic, straight-chain or branched diol having 2 to 20 C atoms
Ar¹, Ar², independently of one another, denote aryl radicals which are each substituted by one or more substituents L and which may additionally be substituted by halogen, alkyl, alkoxy, each having 1 to 5 C atoms, or phenyl, and
L on each occurrence, identically or differently, denotes a hydrophilic radical.

8. A liquid-crystal display according to claim 7, produced by an ODF process.

9. A liquid-crystal display according to claim 7, that is a PS-VA, PS-IPS, PS-FFS, PS-OCB or PS-TN display.

10. A liquid-crystal display according to claim 7, where in the sealant has been cured.

11. A liquid-crystal display according to claim 10, that is a PS-VA, PS-IPS, PS-FFS, PS-OCB or PS-TN display.

* * * * *